(12) United States Patent
Gramnäs

(10) Patent No.: US 6,626,951 B1
(45) Date of Patent: Sep. 30, 2003

(54) LOCKING DEVICE INTENDED AS A FASTENING ELEMENT FOR A PROSTHESIS

(76) Inventor: Finn Gramnäs, Hästskovägen 5, S-511 56 Kinna (SE)

( * ) Notice: Subject to any disclaimer, the term of this patent is extended or adjusted under 35 U.S.C. 154(b) by 0 days.

(21) Appl. No.: 10/009,374

(22) PCT Filed: Jun. 7, 2000

(86) PCT No.: PCT/SE00/01184
§ 371 (c)(1),
(2), (4) Date: Dec. 4, 2001

(87) PCT Pub. No.: WO00/74609
PCT Pub. Date: Dec. 14, 2000

(30) Foreign Application Priority Data
Jun. 8, 1999 (SE) ................................. 9902129

(51) Int. Cl.$^7$ ................................. A61F 2/80
(52) U.S. Cl. .................. 623/33; 623/36; 292/306; 403/325
(58) Field of Search ............... 403/325; 292/306, 292/341.15; 623/33, 36, 38

(56) References Cited

U.S. PATENT DOCUMENTS 2,090,550 A * 8/1937 Pilblad ................. 292/306
3,468,579 A * 9/1969 Tabor ................... 292/306

FOREIGN PATENT DOCUMENTS

| DE | 1142527 | * | 1/1963 | ............... 292/306 |
| WO | WO 94/04101 A1 | | 3/1994 | |
| WO | WO 99/32056 A1 | | 7/1999 | |

OTHER PUBLICATIONS

International Search Report mailed from the Swedish Patent Office on Sep. 26, 2000.
International Preliminary Examination Report mailed from the Swedish Patent Office on Sep. 7, 2001.

* cited by examiner

*Primary Examiner*—David H. Willse
(74) *Attorney, Agent, or Firm*—Gardner Carton & Douglas LLC

(57) ABSTRACT

The present invention provides a locking device intended as a fastening element for prostheses, of the kind in which the prosthesis is attached to a cylindrical member. The locking device includes a housing with a through opening for receiving the cylindrical member and a locking mechanism arranged therein for locking to the cylindrical member in one axial direction thereof. In the housing along the through opening of the housing opposite the locking mechanism there is further arranged a spring-loaded gripping washer with a through opening which is somewhat larger than the diameter of the cylindrical member and which by an axle having a lever arm is brought to an inclined position and grips the cylindrical member and pulls the cylindrical member further into the housing.

8 Claims, 5 Drawing Sheets

LOCKING DEVICE INTENDED AS A FASTENING ELEMENT FOR A PROSTHESIS

TECHNICAL FIELD

The present invention refers to a locking device intended as a fastening element for prostheses, such as leg- or arm prostheses, of the kind in which the prosthesis is to be attached to a cylindrical member such as a pin, an axle, a tube or the like, said locking device comprises a housing with a through opening for receiving said pin or the like and a locking mechanism arranged therein for locking to the pin in one axial direction thereof, and said locking device further comprising activating means for activating and releasing the grip of the locking mechanism to the pin.

BACKGROUND OF THE INVENTION

The locking device can for example be used in such cases where a silicone stocking has been threaded on the arm- or leg stump, said silicone stocking in its bottom part having a plastic cup moulded thereto and said plastic cup having a pin attached thereto. The leg- or arm stump provided with the silicone stocking is inserted into a prosthesis sleeve attached to the prosthesis, said sleeve being provided with a locking device for the pin.

In the international patent application WO 94/04101 there is shown a fastening means intended for a prosthesis, said fastening means being in the form of an inclined washer which by spring force is kept in an inclined position and in this position locks to the pin. The inclination of the washer can be reduced by means of an actuating means, at which the locking to the pin is released.

In the international patent application WO 99/32056 there is shown a locking device for a prosthesis comprising a holder with a ring of balls arranged therein, which by spring action is pressed into a conical seat, at which it is locked to the pin. The ring of balls can be released from the conical seat by means of actuating means.

These locking devices per se function well, but it can sometimes be difficult for the prosthesis wearer to with his own force bring the pin with the silicone stocking and stump connected thereto sufficiently deep enough into the locking device attached to the prosthesis sleeve. This problem can for example occur due to a large amount of soft parts on the arm- or leg stump. The consequence will be instability and a so called pump effect, which means that the prosthesis is displaced up and down on the leg stump for each step that is taken. The risk for stumbling increases since the prosthesis consequently slides down on the leg stump when the prosthesis is lifted from the floor. Injurious compensating behaviour can then occur, for example by lifting the leg higher by means of the hip and raising on tiptoe with the healthy foot in order to get free from the ground.

OBJECT AND MOST IMPORTANT FEATURES OF THE INVENTION

The object of the present invention is to provide a locking device of the kind mentioned above, which in an effective way helps the prosthesis wearer to pull the pin and by that the silicone stocking/body part deeper into the prosthesis sleeve/locking device. This has been provided by the fact that in the housing along the opening opposite the locking mechanism there is further arranged a gripping member in the form of a spring-loaded washer with a through opening which is somewhat larger than the diameter of the pin and which by means of actuating means can be brought to a tilted position and grip the pin and by that pull this further into the locking device.

Further features of the invention are understood from the following description and the dependant claims.

DESCRIPTION OF DRAWINGS

The invention will in the following be closer described with reference to a pair of embodiments shown in the accompanying drawings.

FIG. 6 is a vertical section taken perpendicularly with respect to FIGS. 2–4 and showing the locking device in the same position as in FIG. 4a.

DESCRIPTION OF THE EMBODIMENTS

Figure 1:
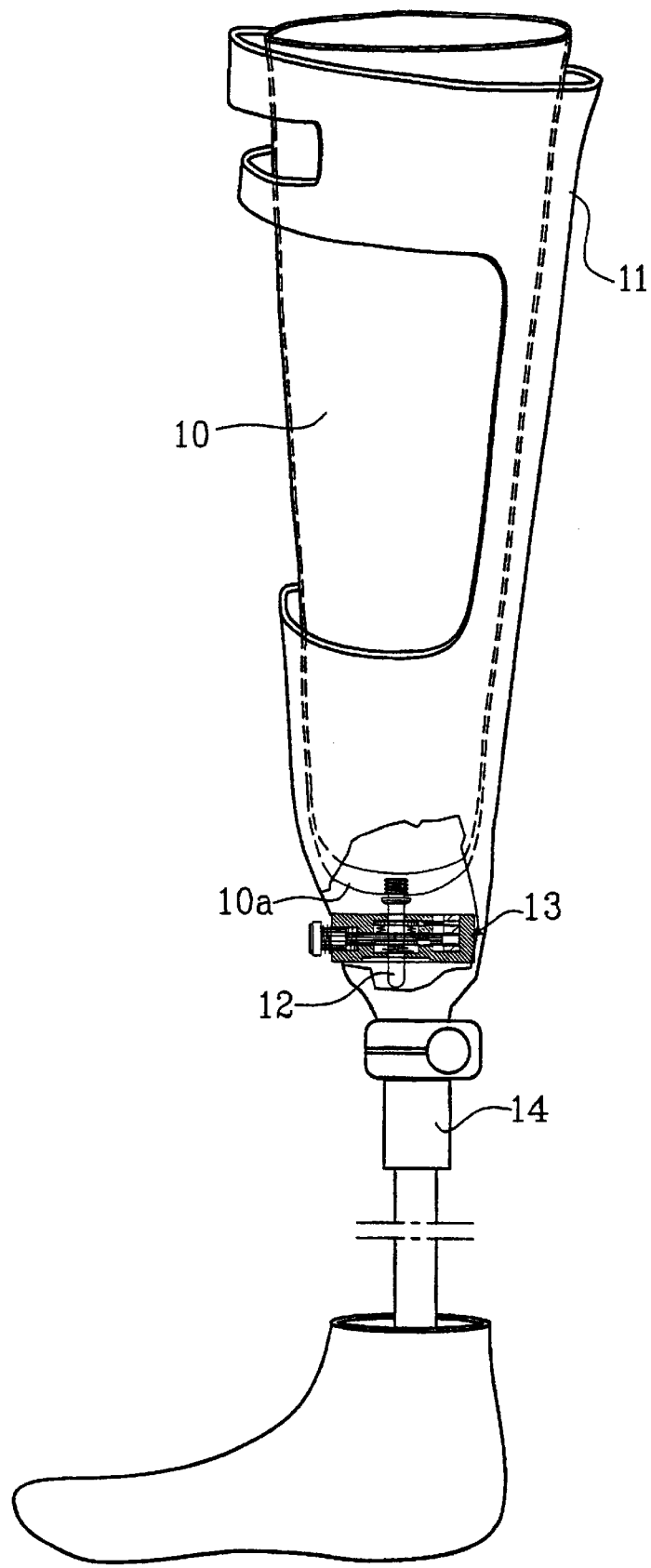
FIG. 1 shows a leg prosthesis provided with a locking device according to the invention.

In FIG. 1 there is shown a silicone stocking 10 intended to be passed on an amputated leg. In the bottom of the silicone stocking 10 there is moulded a plastic cup 10a in which a cylindrical pin 12 is screwed. The amputated leg stump provided with the silicone stocking 10 is slipped into a prosthesis sleeve 11. Said sleeve 11 is provided with a locking device 13 for the pin 12 and is connected to a prosthesis, in the example shown a leg prosthesis 14.

Figure 4A:
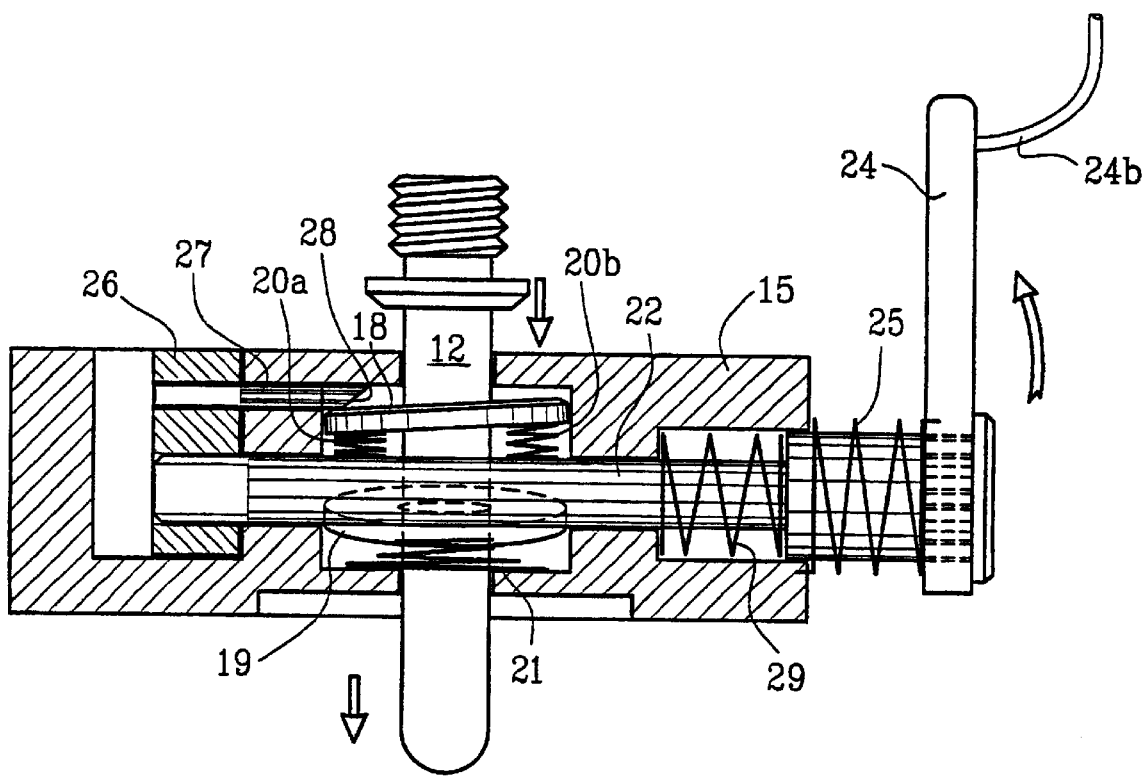
FIG. 4a is a corresponding section as FIGS. 2 and 3 but showing a position in which the gripping member is activated.
Figures 4B, 4C:
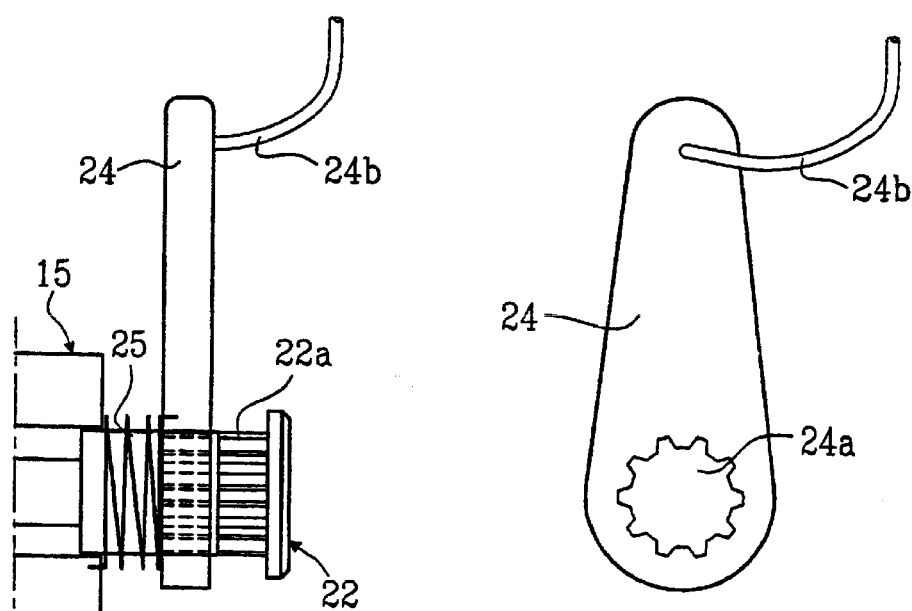
FIG. 4b shows the operating member for m maneuvering the gripping member in a position in which it can be rotated with respect to the axle.
FIG. 4c shows the operating member in a front view.
Figure 5A:
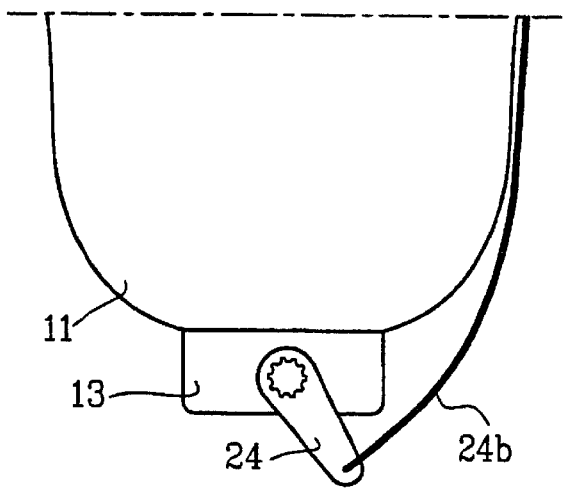
FIGS. 5a and b show schematically two prostheses sleeves of two different sizes and where the operating member has been angled in different positions for permitting a simple maneuvering for the prosthesis wearer.
Figure 5B:
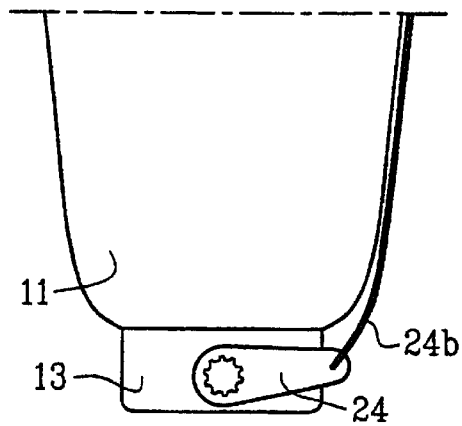
Figure 6:
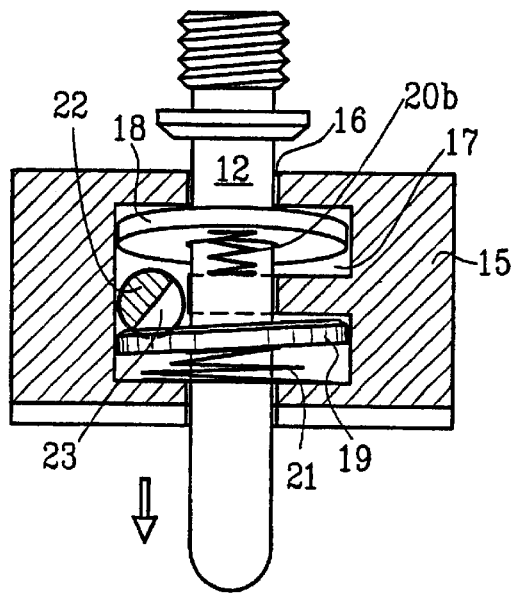
Figure 7:
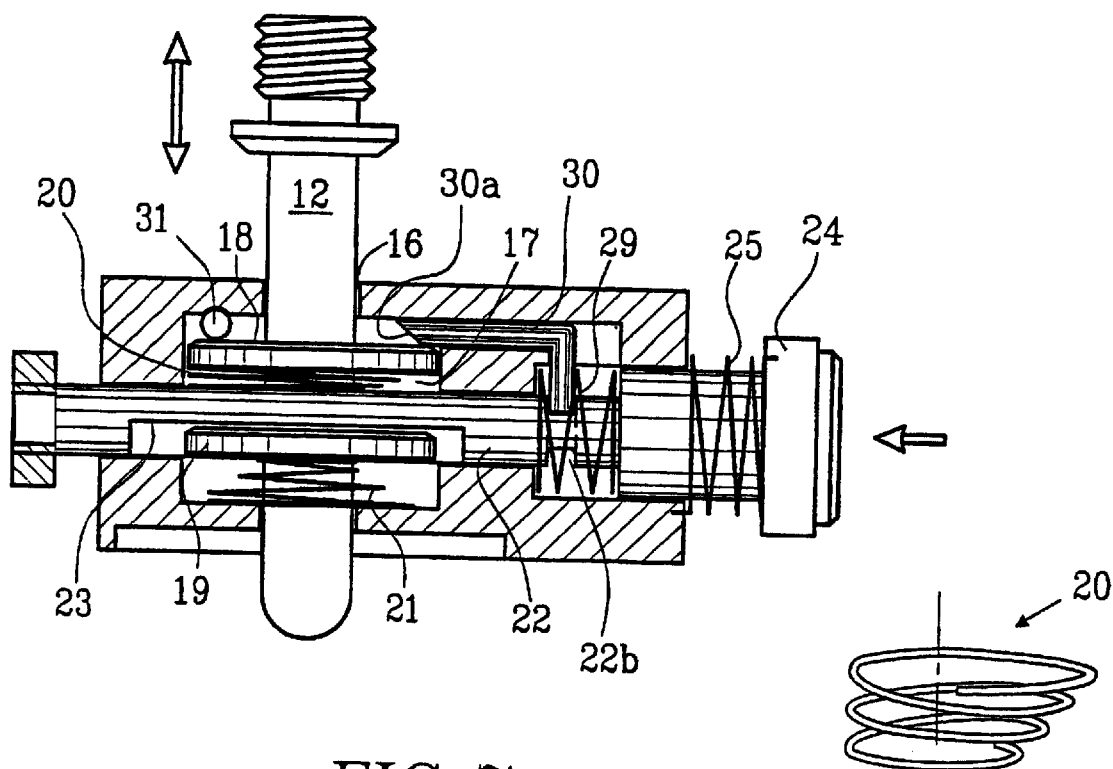
FIG. 7 is a vertical section through another embodiment of the locking device in released connecting position.

The locking device 13 which is shown more in detail in FIGS. 2–5, comprises a housing 15, with a through opening 16 for receiving the pin 12. The opening 16 is provided with an enlarged portion 17, in which a first washer is arranged, the locking washer 18, and a second washer, the gripping washer 19. The locking washer 18 is provided with a through opening which is somewhat larger than the diameter of the pin 12 and is spring-loaded with a spring 20a,b. By pressing one edge of the locking washer 18 downwards the washer will tilt and locks to the pin 12 so that this can not be pulled out of the locking device 13. This locking function is disclosed in WO 94/04101. The spring-loading of the locking washer 18 can be provided by means of two springs 20a, b as is shown in FIGS. 1–5 or by one spring 20 as is shown in FIGS. 6–7.

Also the gripping washer 19 is spring-loaded with a spring 21 and is provided with a through opening which is somewhat larger than the diameter of the pin 12. One edge of the gripping washer 19 rests in a recess 23 in an axle 22 which extends through the housing 15 across the opening 16 offset with respect thereto. The recess 23 has such a length with respect to the size of the gripping washer 19 that a certain axial movement of the axle 22 is permitted. By rotating the axle 22 the gripping washer 19 is brought out of the recess 23 at which the axle 22 will press down one edge of the gripping washer 19 against the action of the spring 21 and thus tilt the gripping washer 19 and cause the gripping washer 19 to grip the pin 12 and draw the pin 12 further into the opening 16 of the locking device 13. This will be described more in detail below.

The axle 22 thus forms an actuating means for the gripping washer 19 for the activation and tilting thereof in order to grip the pin 12 and draw the pin 12 deeper into the locking device 13. The axle 22 projects outside the housing 15 and is provided with a maneuvering means 24 at its end located outside the housing 15. The rotational movement of the axle 22 takes place against the action of a torsion spring 25 attached to and extending between the housing 15 and the maneuvering means 24. The maneuvering means 24 preferably consists of a lever arm. The maneuvering means 24 is preferably provided with a hole 24 having a star-shaped cross-section intended to be unrotatably connected to the outer end of the axle 22, which has a corresponding star-shaped cross-section by the fact that it is provided with splines 22a. To the maneuvering means 24 there is further connected a wire 24b which easily can be gripped by the prosthesis wearer, who then easily can rotate the maneuvering means. The maneuvering means 24 can against the action of the spring 25 be displaced inwards on the axle 22, so that it is brought out of engagement with the splines 22a, at which it can be angled with respect to the axle 22, and positioned so that it gets a correct angle with respect to the wire 24b depending on the size of the prosthesis sleeve 11. This is best illustrated in FIGS. 5a and b which show two different sizes of prosthesis sleeves 11, at which the maneuvering means 24 has been angled in different positions with respect to the wire 24b for a comfortable maneuver.

The axle 22 also forms a part of the maneuvering mechanism for activating and releasing the grip of the locking washer 18 to the pin 12. The axle 22 is thus at its inner end located in the housing 15 remote from the opening 16, rigidly in its longitudinal direction and via a plate 26 rotatably connected to a peg 27. The axle 22 can be threaded 22c into the plate 26 or in some other way be rotatably but rigidly in its longitudinal direction connected to said plate 26. The peg 27 has a chamferred edge 28 intended to cooperate with the locking washer 18. The peg 27 can thus with its chamferred edge 28 be brought to slide up on the locking washer 18 and press one edge thereof downwards against the action of the spring 20a in order to tilt the locking washer 18 and lock it to the pin 12. The movement of the peg 27 towards and away from the locking washer 18 is provided by means of the axle 22, the axial movement thereof being spring-loaded by a compression spring 29.

Figure 2:
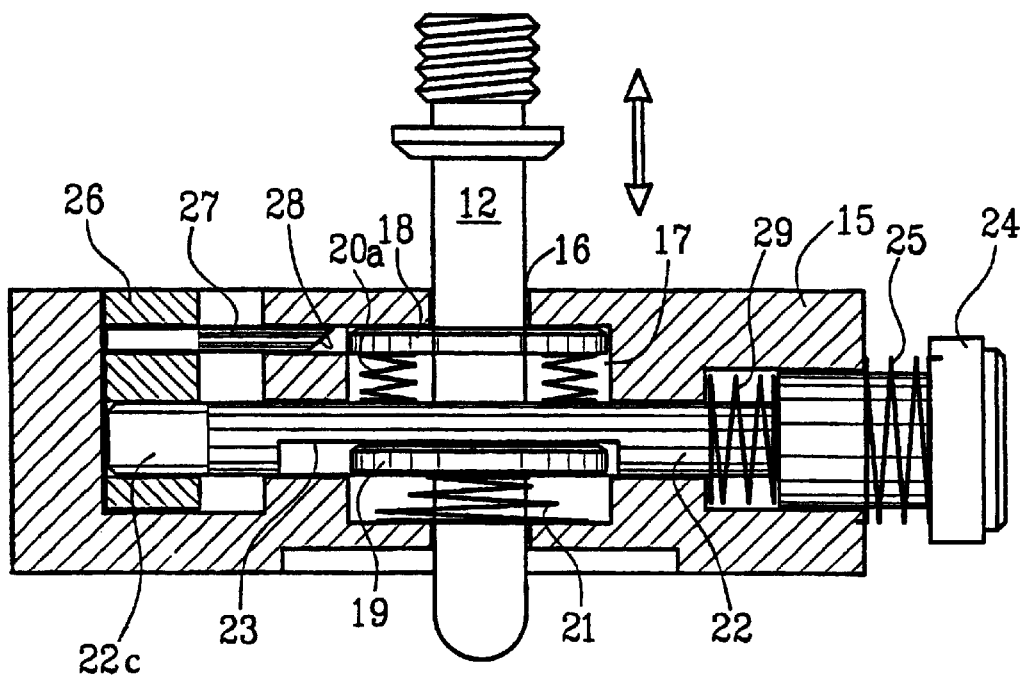
FIG. 2 is a vertical section through an embodiment of the locking device in released connecting position.

In FIG. 2 the locking device 13 is shown in an open position, in which the axle 22 against the action of the compression spring 29 has been pushed further into the housing 15. The chamferred edge 28 of the peg 27 has now been brought out of engagement with the locking washer 18, which then by the spring 20a is held in a straight non-tilted position. The pin 12 can now freely be brought through the opening of the locking washer 18 in both directions. The gripping washer 19 is also by the spring 21 held in a straight position in order to permit the movement of the pin 12.

Figure 3:
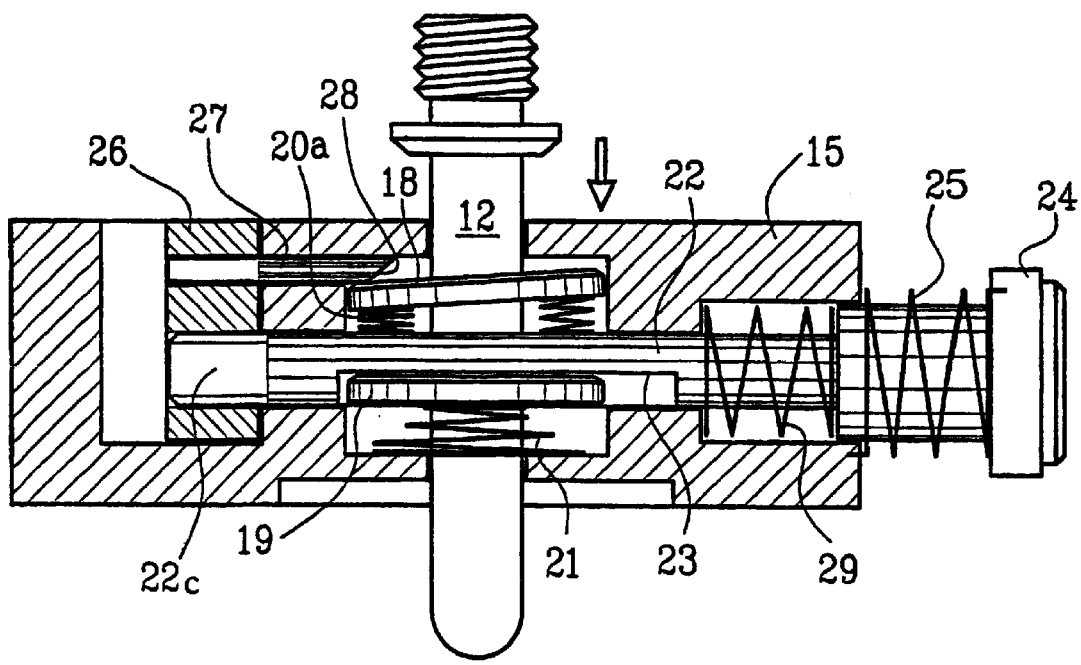
FIG. 3 is a corresponding section through the locking device in locked position.

When the axial pressure on the axle 22 ceases the axle will by the compression spring 29 be pressed back a certain distance in the direction out of the housing 15 to the position shown in FIG. 3. The peg 27 will then with its chamferred edge 28 slide up on the locking washer 18 and press one edge thereof downwards against the action of the spring 20a. The locking washer 18 will then tilt and lock to the pin 12 so that it can not be pulled out. On the other hand the pin 12 can be brought further into and be positioned in an optional position in the housing 15. This is shown in FIGS. 3–5.

The first spring 20a serves the purpose of holding the locking washer 18 in contact with the contact surface towards the peg 27, while the second spring 20b ensures the locking function of the locking washer 18. The spring pressure of the first spring 20a should be greater than that of the second spring 20b, in order to provide a play free locking function, and prevent that the locking washer 18 is brought along by the pin 12 downwards until the spring 20a has been completely compressed.

In order to permit rotational movement between the pin 12 and the locking device 13 in locked position the contact surfaces between the locking washer 18 on one hand and the housing 15, the peg 27 and the springs 20a,b on the other hand should be of a low friction type, such as roll- or slide. This is more fully described in WO 94/04101. The contact surfaces between the gripping washer 19 and the axle 22 and the spring 21 should also be low fraction sliding- or rolling surfaces.

Figure 8:
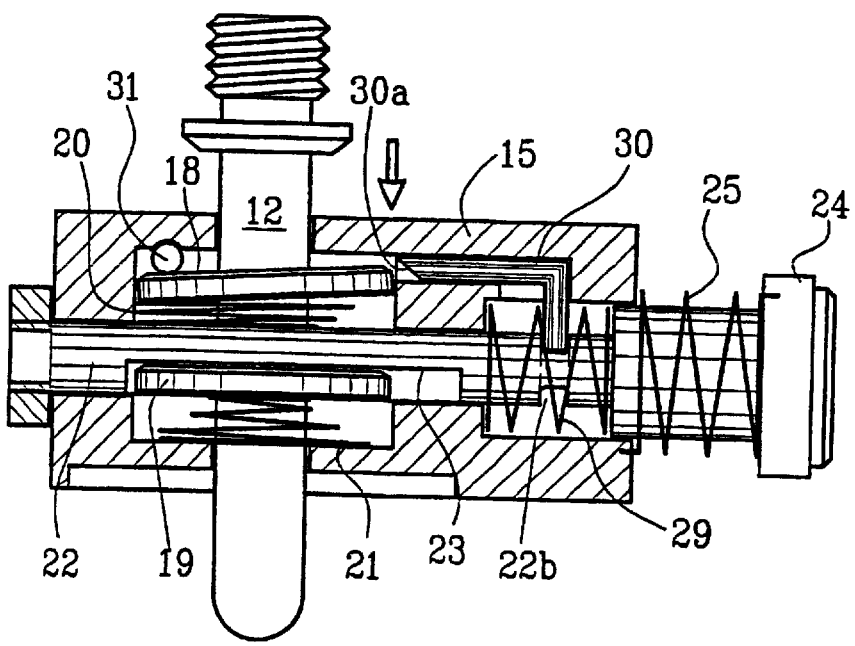
FIG. 8 is a corresponding section through the locking device according to FIG. 7 in locked position.

In FIGS. 7 and 8 there is shown a modified embodiment of the maneuvering device which activates the locking function of the locking washer 18. A ball 31 fitted into a recess in the housing presses down one edge of the locking washer 18 for tilting it. At the same time the ball 31 makes a roll contact surface between the locking washer 18 and the housing 15. Instead of two springs it is only one spring 20 that acts on the locking washer 20. This spring should be dimensioned so that a higher spring pressure is achieved on the side of the locking washer 18 that is located just opposite the ball 31, i.e., the contact surface between the locking washer 18 and the housing 15. By this there is prevented a play in the locking function in a corresponding manner as is disclosed above with respect to the springs 20a,b.

A peg 30 connected to the axle 22 is arranged to act upon the opposite edge of the washer 18. When the knob 24 and the axle 22 connected thereto is pressed inwards against the action of the compression spring 29 the peg 30 with its chamferred surface 30a will slide up on the washer and press down the opposite edge thereof, at which the washer 18 takes a straight position in which the pin 12 freely can be brought out of the locking device 13. When the pressure on the knob 24 ceases the axle 22 will return to its outer position in which the chamferred edge 30a of the peg 30 has slid off the washer 18, at which this is tilted to its locking position in which the pin 12 is prevented from being pulled out. The peg 30 is not unrotatably connected to the axle 22, but runs in an annular groove 22b therein, so that the rotational movement of the axle 22 does not effect the peg 30.

It is important to note that the locking washer 18 in its locking position only locks the pin 12 in the pulling out direction. The pin 12 can on the other hand also in locking position be brought deeper into the locking device 13.

The amputated leg stump is often swollen in the morning and can then not be passed completely down into the prosthesis sleeve 11 but will gradually sink down during the day. The locking device 13 according to the invention permits this since the locking occurs completely without play. With this is meant that every movement of the pin 12 downwards in the locking device 13 will be caught thereby and the locking device 13 immediately locks if the pin 12 moves in the opposite direction, locking direction.

Sometimes it can however be difficult for the prosthesis wearer to with his/her own force bring the pin 12 sufficiently deep into the locking device 13. This problem can among other thing occur due to a great amount of soft parts on the arm or leg stump. The locking device 13 according to the invention thus is provided with means for aiding in drawing the silicone stocking 10 and the body part deeper into the prosthesis sleeve 11. This is made by bringing the pin 12 deeper into the locking device 13. Said means comprises the gripping washer 19, which as described above by means of a rotational movement of the axle 22 is brought to tilt, at which it grips the pin 12 and forces this a distance deeper into the housing 15. This is shown in FIGS. 4 and 5. The spring 25 then pulls the axle 22 back to its position shown in FIG. 3, in which the gripping washer 19 rests in the recess 23 again. The pin 12 however remains in its pulled down-position since the locking washer 18 prevents it from moving back upwards. By rotating the axle 22 once more to the position shown in FIGS. 4 and 5 the pin 12 is pulled a further distance down into the housing 15. It is thus possible to gradually pull the pin 12 down into the housing 15 by tilting the axle 22 between the positions shown in FIG. 3 and FIGS. 4–5.

It is of course possible to modify the mechanisms that actuates the functions of the gripping washer 19 and the locking function of the locking washer 18 and to make them completely separate from each other.

The locking mechanism described above and shown in the drawings which is in the form of a tiltable locking washer 18 may be replaced by principally any optional locking mechanism which locks to the pin 12 in one direction, but permits movement in the opposite direction. One such example is the locking device in the form of a ring of balls that can be pressed into a conical seat, as is shown in the international patent application no. PCT/SE98/02170.

Further modifications of the invention are possible within the scope of the claims.

What is claimed is:

1. A locking device intended as a fastening element for prostheses, of the kind in which the prosthesis is to be attached to a cylindrical member, said locking device comprises a housing with a through opening for receiving said cylindrical member and a locking mechanism arranged therein for locking to the cylindrical member in one axial direction thereof, and said locking device further comprising a maneuvering means for activating and releasing the grip of the locking mechanism to the cylindrical member, characterized in, that in the housing along the opening opposite the locking mechanism there is further arranged a gripping member in the form of a spring-loaded washer with a through opening which is larger than the diameter of the cylindrical member and which by an actuating means can be brought to a tilted position and grip the cylindrical member and pull the cylindrical member further into the housing.

2. The locking device according to claim 1, characterized in, that the actuating means comprises an axle extending across the opening of the housing, said axle having a recess in which one edge of the spring-loaded gripping washer rests, wherein by rotating the axle said axle is brought to press one edge of the washer downwards and thus tilt the washer and make the washer grip the cylindrical member.

3. The locking device according to claim 2, characterized in, that the axle is connected to the maneuvering means in such a way that an axial movement of the axle actuates the locking of the locking mechanism to the cylindrical member while a rotation of the axle actuates the function of the gripping washer.

4. The locking device according to claim 1, characterized in, that the maneuvering means for activating and releasing the grip of the locking mechanism to the cylindrical member is separate from the function of the actuating means for the gripping member.

5. The locking device according to claim 1, characterized in, that said locking mechanism comprises a spring-loaded locking washer having an opening which is larger than the diameter of the cylindrical member and which against the action of said spring by means of a maneuvering member can be brought to tilt and lock to the cylindrical member, wherein the maneuvering member is provided with a low friction contact surface towards the locking washer which permits rotation of the cylindrical member in the housing of the locking device also in the locked position of the cylindrical member.

6. The locking device according to claim 5, characterized in, that the maneuvering member comprises a peg provided with a chamferred edge which can be brought to slide up on one edge of the locking washer and cause tilting of the locking washer.

7. The locking device according to claim 5, characterized in, that the maneuvering member is connected to the axle of the actuating means so that an axial movement of said axle causes a displacement of the maneuvering member in and out of engagement with the locking washer.

8. The locking device according to claim 7, characterized in, that the maneuvering member comprises a peg provided with a chamferred edge which can be brought to slide up on one edge of the locking washer and cause tilting of the locking washer.

* * * * *